(12) United States Patent
Sokel et al.

(10) Patent No.: US 10,426,922 B2
(45) Date of Patent: Oct. 1, 2019

(54) MEDICAL APPARATUS AND METHOD OF MAKING THE SAME

(71) Applicant: W. L. Gore & Associates, Inc., Newark, DE (US)

(72) Inventors: Justin W. Sokel, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1248 days.

(21) Appl. No.: 14/280,402

(22) Filed: May 16, 2014

(65) Prior Publication Data

US 2014/0257246 A1   Sep. 11, 2014

Related U.S. Application Data

(63) Continuation of application No. 13/297,036, filed on Nov. 15, 2011, now Pat. No. 8,756,789.

(60) Provisional application No. 61/414,270, filed on Nov. 16, 2010.

(51) Int. Cl.
   *A61M 25/00*   (2006.01)
   *A61F 2/962*   (2013.01)
   *A61F 2/97*    (2013.01)

(52) U.S. Cl.
   CPC ......... *A61M 25/0067* (2013.01); *A61F 2/962* (2013.01); *A61F 2/97* (2013.01); *A61M 25/0069* (2013.01); *Y10T 29/49863* (2015.01); *Y10T 29/49908* (2015.01); *Y10T 29/49913* (2015.01); *Y10T 29/49934* (2015.01)

(58) Field of Classification Search
   CPC .......... A61M 25/0067; A61M 25/0069; A61F 2/962; A61F 2/97; A61F 2/95; A61F 2/958; A61F 2002/9511; Y10T 29/49913; Y10T 29/49934; Y10T 29/49863; Y10T 29/49908
   See application file for complete search history.

(56) References Cited

U.S. PATENT DOCUMENTS

| | | | |
|---|---|---|---|
| 5,690,644 A * | 11/1997 | Yurek | A61F 2/95 606/198 |
| 6,425,898 B1 * | 7/2002 | Wilson | A61F 2/95 606/108 |
| 6,726,701 B2 | 4/2004 | Gilson et al. | |
| 7,117,693 B1 | 10/2006 | Nova | |
| 7,303,213 B2 | 12/2007 | Rytter | |

(Continued)

FOREIGN PATENT DOCUMENTS

| | | |
|---|---|---|
| GB | 1332062 | 10/1973 |
| WO | 94/15549 | 7/1994 |

(Continued)

*Primary Examiner* — Robert A Lynch (57) ABSTRACT

A catheter assembly includes a catheter having a proximal end and a distal end; an expandable device releasably attached to the catheter near the distal end; a generally tubular constraining sleeve extending around and compressing the device to an outer peripheral dimension suitable for endoluminal delivery; a tip fixedly secured to the distal end of the catheter; and a bridge member disposed between the tip and the expandable device so as to fill a gap therebetween as the catheter assembly is bent during endoluminal delivery of the expandable device to a treatment site.

21 Claims, 7 Drawing Sheets

(56) References Cited

U.S. PATENT DOCUMENTS

| | | |
|---|---|---|
| 7,758,624 B2 | 7/2010 | Dorn et al. |
| 7,780,716 B2 | 8/2010 | Pappas et al. |
| 2003/0233037 A1 | 12/2003 | Bencini |
| 2004/0015224 A1* | 1/2004 | Armstrong ................ A61F 2/95 623/1.12 |
| 2008/0132989 A1 | 6/2008 | Snow et al. |
| 2008/0140175 A1 | 6/2008 | Boucher et al. |
| 2009/0276027 A1* | 11/2009 | Glynn ...................... A61F 2/95 623/1.11 |
| 2009/0281617 A1 | 11/2009 | Cottone et al. |
| 2010/0152574 A1 | 6/2010 | Erdman et al. |

FOREIGN PATENT DOCUMENTS

| | | |
|---|---|---|
| WO | 2006/105500 | 10/2006 |
| WO | 2009/134801 | 11/2009 |

* cited by examiner

MEDICAL APPARATUS AND METHOD OF MAKING THE SAME

BACKGROUND

Field

The present disclosure relates to catheter-based systems used to deliver medical devices.

Discussion of the Related Art

Various medical devices require catheter based delivery systems. Such medical devices include implantable, diagnostic and therapeutic devices. Common implantable, endovascular devices can include stents, stent grafts, filters, occluders, sensors and other devices. Endovascular devices are commonly advanced through the native vasculature to a treatment site by the use of a flexible catheter. When properly positioned at the treatment site the device (in the case of a stent) can be expanded to appose the vasculature. The device can then be released from the catheter allowing the catheter to be withdrawn from the vasculature. It is desirable to pre-compact endovascular devices into small delivery profiles in order to minimize vascular trauma and enhance maneuverability through torturous anatomies. A highly compacted device is often relatively stiff and is therefore difficult to bend into a small radius. A soft, flexible "olive" or tip is commonly positioned distal to the compacted device at the leading end of the delivery catheter, again to minimize vascular trauma and to enhance the positioning accuracy. As the device is advanced through a curved vessel, the junction between the relatively stiff compacted device and the soft flexible tip can "open up" presenting a gap.

It remains desirable to have a device delivery system incorporating a means to cover any potential gap between the compacted device and a leading catheter tip.

SUMMARY

In one example ("Example 1"), a catheter assembly comprise a catheter having a proximal end and a distal end, an expandable device releasably attached to the catheter near the distal end and maintained toward an outer peripheral dimension suitable for endoluminal delivery, a tip fixedly secured to the distal end of and generally coaxial with the catheter, and a bridge member generally coaxial with the catheter and compressed between the tip and the expandable device to fill a gap therebetween.

In another example ("Example 2") further to Example 1, the bridge member is generally annular and includes a tapered surface radially engaging at least one of the expandable device and constraining sleeve.

In another example ("Example 3") further to Example 2, the tapered surface outwardly radially tensions at least one of the expandable device and constraining sleeve.

In another example ("Example 4") further to Example 3, the tapered surface is generally frustoconically shaped.

In another example ("Example 5") further to Example 1, the catheter includes a lumen extending between the proximal and distal ends. The catheter assembly also includes a tubular member extending through the lumen and having an end fixedly secured to the tip.

In another example ("Example 6") further to Example 5, the tubular member includes a guidewire lumen extending axially therethrough.

In another example ("Example 7") further to Example 6, the bridge member is generally annular and includes a bore which receives the tubular member therethrough.

In another example ("Example 8") further to Example 1, the bridge member fills a gap between the tip and the expandable device and provides a transition therebetween upon bending of the distal end of the catheter during deployment at an angled treatment site.

In another example ("Example 9") further to Example 1, the bridge member is elastically deformed upon compression between the tip and the expandable device.

In another example ("Example 10") further to Example 9, the bridge member is axially movable with respect to the catheter.

In another example ("Example 11") further to Example 10, at least a portion of the bridge member is fixedly secured to the tip or catheter.

In another example ("Example 12") further to Example 5, a portion of the bridge member is fixedly secured to the tubular member so that a remaining portion of the bridge member is axially movable with respect to the catheter.

In another example ("Example 13") further to Example 1, the tip includes a bore generally axially aligned with the guidewire lumen to allow a guidewire to be fed through the catheter and tip.

In another example ("Example 14") further to Example 1, the bridge member includes a frustoconically shaped leading surface that faces the tip, which upon compression between the expandable device and tip provides a transition between the tip and the constraining sleeve.

In another example ("Example 15") further to Example 1, the bridge member includes portions of varying durometer.

In another example ("Example 16") further to Example 1, the bridge member includes a generally tubular shaped side wall and includes a wire frame coupled thereto to help the side maintain the gap between the tip and the device as the catheter assembly is bent during endoluminal delivery of the expandable device to a treatment site.

DETAILED DESCRIPTION

Figure 1:
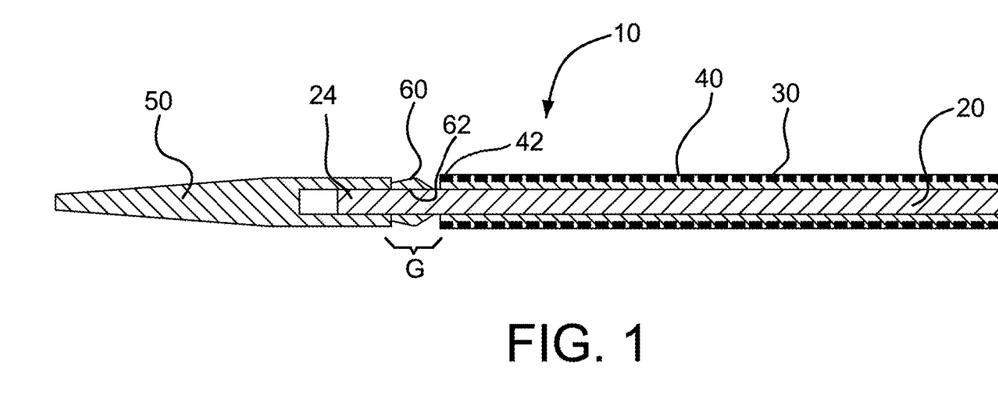
FIG. 1 is a cross-sectional view of a catheter assembly in accordance with various embodiments with a bridging member shown in an uncompressed state between a distal tip and device of the catheter assembly.
Figure 2:
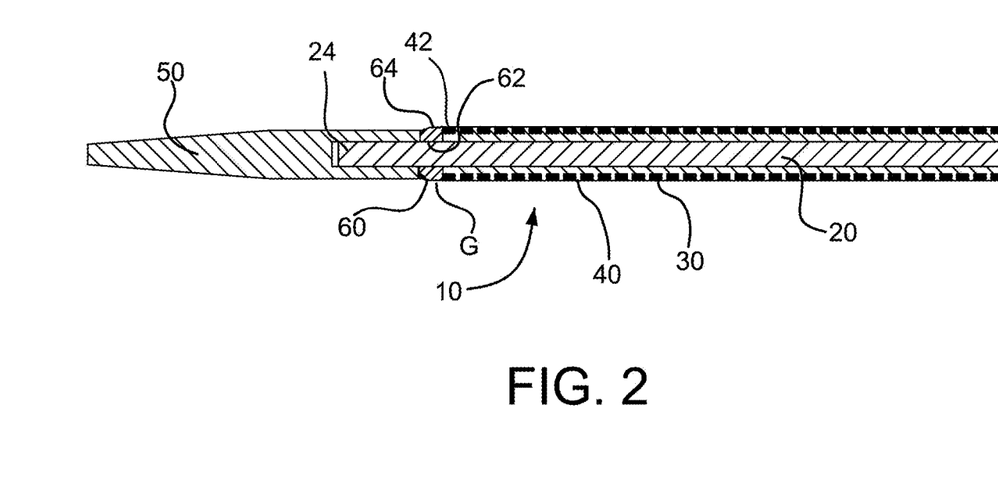
FIG. 2 is a cross-sectional view of the catheter assembly in FIG. 1 with the bridging member shown in a compressed state between the distal tip and catheter assembly.

Referring to FIGS. 1 and 2, a catheter assembly in accordance with various embodiments is shown and generally indicated at 10. The catheter assembly 10 includes a catheter 20, an expandable device 30, a generally tubular restraining member or "constraining sleeve" 40 and a tip 50. The catheter 20 extends longitudinally between opposite proximal 22 and distal 24 ends. The expandable device 30 is releasably attached to the catheter 20 near the distal end 24 of the catheter 20. The constraining sleeve 40 is disposed around and compresses the device 30 to an outer peripheral dimension suitable for endoluminal delivery to a treatment site in a patient. The constraining sleeve 40 has a distal end 42 that faces the distal end 24 of the catheter 20. Examples of restraining members or constraining sleeves for releasably maintaining expandable devices in a collapsed state for endoluminal delivery can be found in U.S. Pat. No. 6,352,561 to Leopold et al, the content of which is incorporated herein by reference in its entirety. Described in greater detail below, the catheter assembly 10 further includes a bridge member 60 disposed generally between the tip 50 and the expandable device 30 to fill a gap therebetween.

Figure 3:
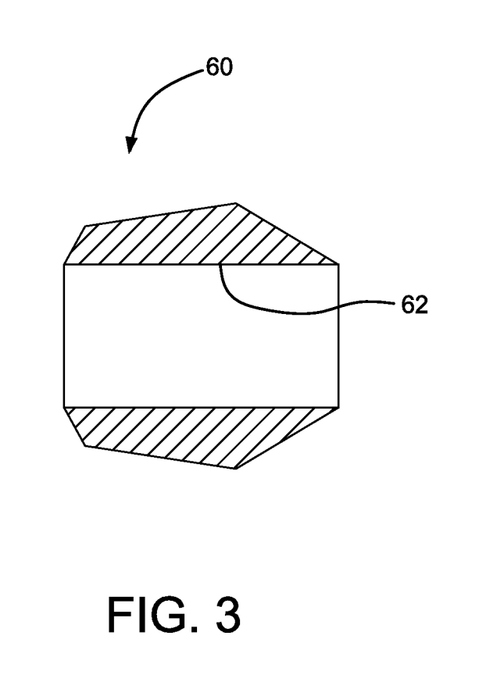
FIG. 3 is a cross-sectional view of the bridging member of FIG. 1 in the uncompressed state.
Figure 4:
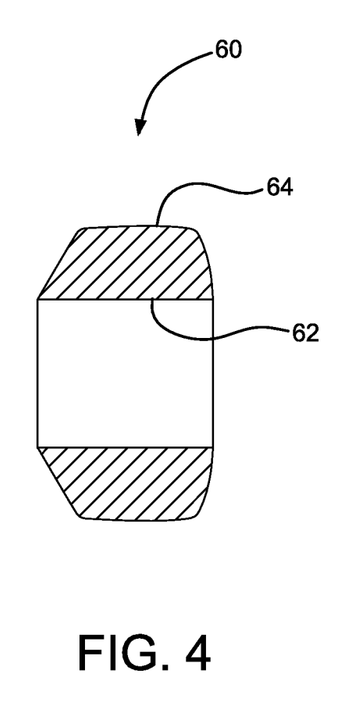
FIG. 4 is a cross-sectional view of the bridging member of FIG. 1 in the compressed state.

In FIG. 1, the bridge member 60 is shown positioned along a gap "G" between the tip 50 and the device 30. The bridge member 60, as shown, is not yet fully assembled to the catheter assembly 10 and is in an uncompressed state (also illustrated in FIG. 3). During assembly of the catheter assembly 10, the device 30 is positioned along the catheter 20 and compressed or crushed onto the catheter by the constraining sleeve 40 so as to have an outer peripheral dimension suitable for endoluminal delivery. The bridge member 60 includes a bore 62 through which the distal end 24 of the catheter 20 is inserted. The tip 50 is then placed onto the distal end 24 of the catheter 20. The tip 50 is pressed axially toward the device 30, and the bridge member 60 is compressed generally axially between the tip 50 and the device 30, as shown in FIG. 2. The tip 50 is fixedly secured to the distal end 24 of the catheter 20 and thereby retains the bridge member 60 in the compressed state (also illustrated in FIG. 4). The tip 50 may be fixedly secured to the distal end 24 of the catheter 20 by a variety of fixing methods, such as by using UV-cured adhesives, ultrasonic welding, reflow bonding, press fits, or other joining methods known in the art.

In one embodiment, the bridge member 60 is compressed elastically between the tip 50 and the device 30 so that as the catheter assembly 10 is bent, such as during endoluminal delivery, the bridge member 60 continues to fill the gap between the tip 5 and the device 30 as well as maintain a generally continuous, transitional surface 64 therebetween. More specifically, as the catheter assembly 10 is bent, the bridge member 60 is further compressed along an inner curve of the bend and at the same time allowed to expand or relax along an outer curve of the bend.

Figure 5:
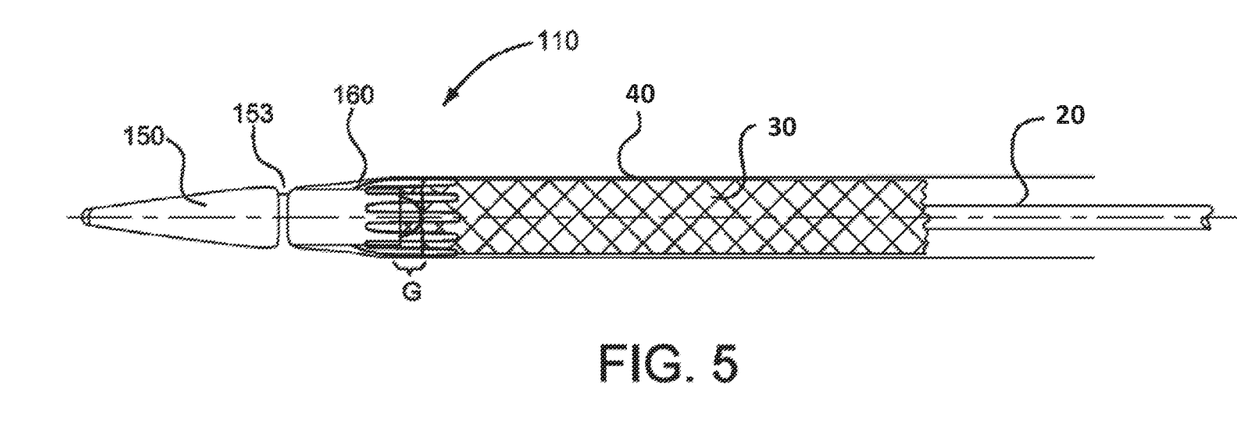
FIG. 5 is a side view of a catheter assembly in accordance with various embodiments.
Figure 6:
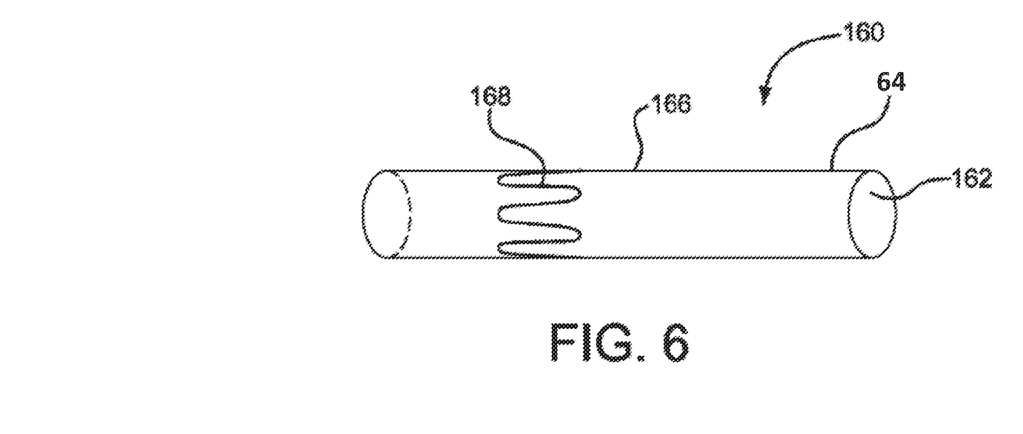
FIG. 6 is a perspective view of a bridging member of the catheter assembly shown in FIG. 5.

In FIGS. 5 and 6, an alternative embodiment of a catheter assembly is shown and generally indicated at 110. The catheter assembly 110 of this embodiment includes a generally tubular bridge member 160 having a lumen or bore 162 defined by a generally cylindrical side wall 166. The side wall 166 may be constructed of ePTFE, or other materials such as FEP, PET, or other medical grade flexible polymers. The bridge member 160 also includes a wire frame 168. The wire frame 168 may be formed from Nitinol. Alternatively, the wire frame may be formed from L605, 304V, MP35N, 316L, or any other medical grade allow. The wire frame 168 may have a generally sinusoidal shape extending peripherally about the side wall 166. The wire frame may also be formed into other shapes depending on the specific treatment needs.

Referring specifically to FIG. 5, the tip 150 may include a circumferential groove 153 onto which the bridge member 160 can be coupled or secured to the tip 150. For example, a releasable shrink tube may be applied about the bridge member 160 along the groove 153 to secure the bridge member 160 to the tip 150.

Figure 7:
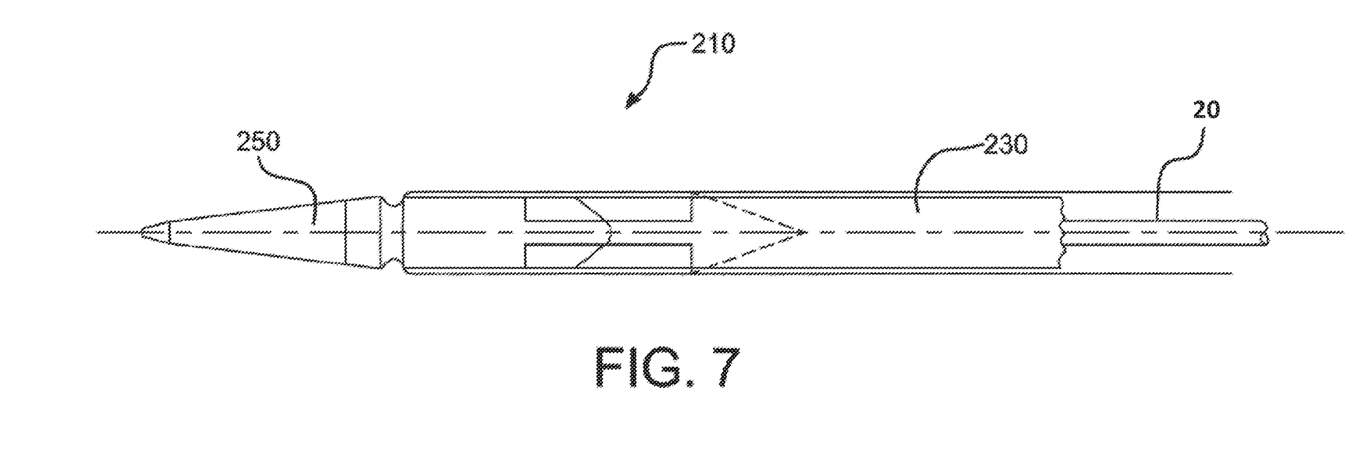
FIG. 7 is side view of a catheter assembly according to various embodiments.
Figure 8:
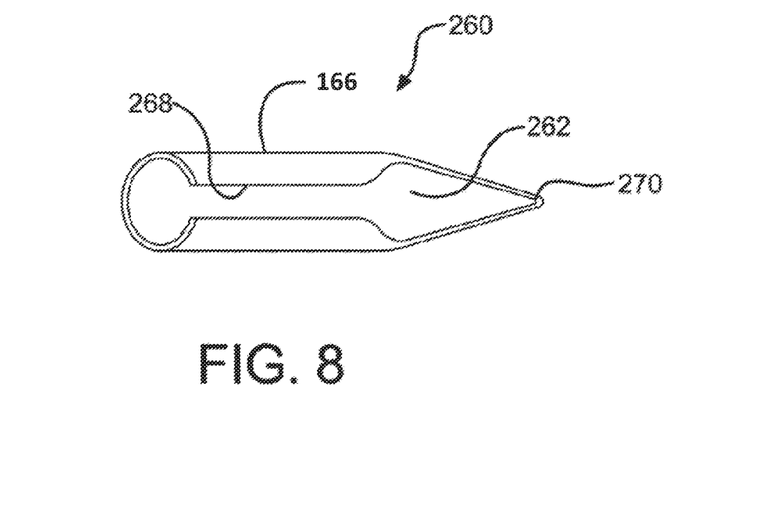
FIG. 8 is a perspective view of a bridging member of the catheter assembly shown in FIG. 7.

In FIGS. 7 and 8, another alternative embodiment of a catheter assembly is shown and generally indicated at 210. The catheter assembly 210 of this embodiment includes a generally cylindrical or tube shaped bridge member 260 having a longitudinally extending slot 268. The bridge member 260 is formed from a metal or metal alloy, such as Nitinol, L605, 304V, MP35N, 316L, or any other medical grade allow. In assembly, the slot 268 allows the bridge member 260 to be expanded radially and elastically to allow insertion of a proximal end of the tip 250 through the bridge member lumen 262. The bridge member 260 is then allowed to return toward its untensioned state and contract toward its untensioned dimension, thereby coupling the bridge member 260 to the tip 250. As in the previous embodiments, the bridge member 260 fills the gap between the tip 250 and the device 230, even as the catheter assembly 210 is bent during endoluminal delivery. The bridge member 260 includes a generally pointed or narrowing proximal tip 270 that facilitates retraction of the catheter assembly 210 through a sheath (not shown).

Figure 9:
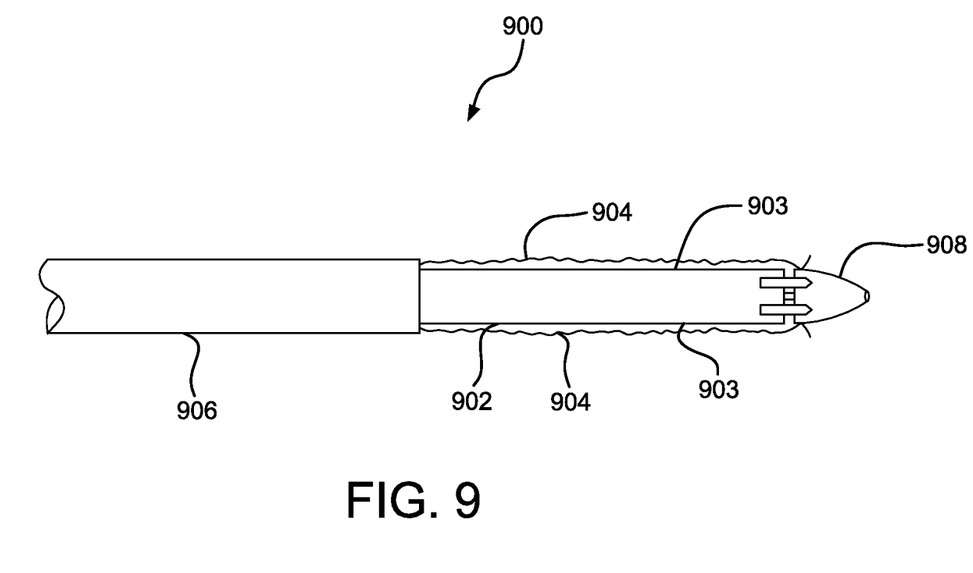
FIG. 9 is a perspective view of a bridging member in accordance with various embodiments.
Figure 10:
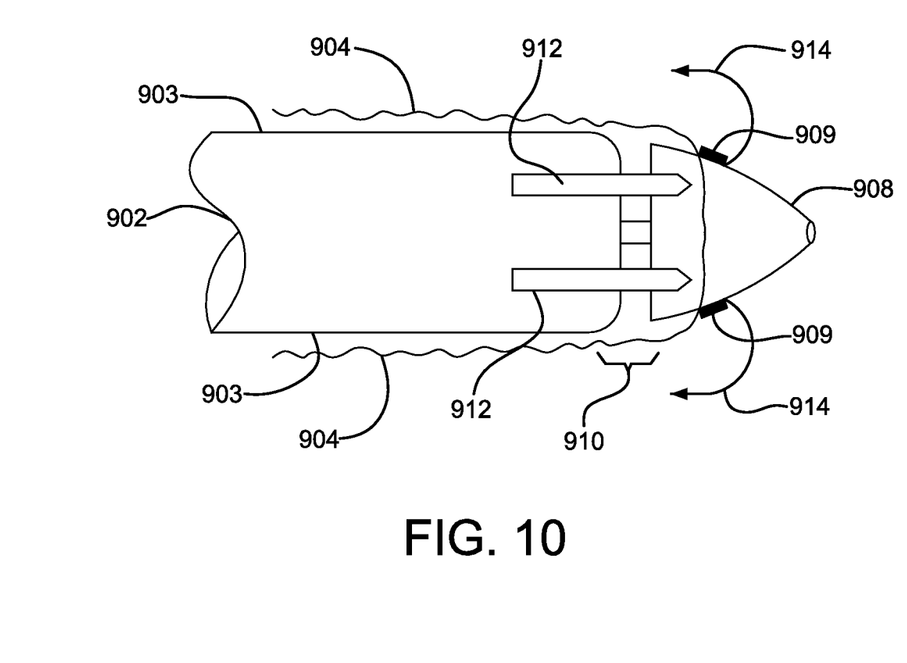
FIG. 10 is an enlarged perspective view of the bridging member in FIG. 9.
Figure 11:
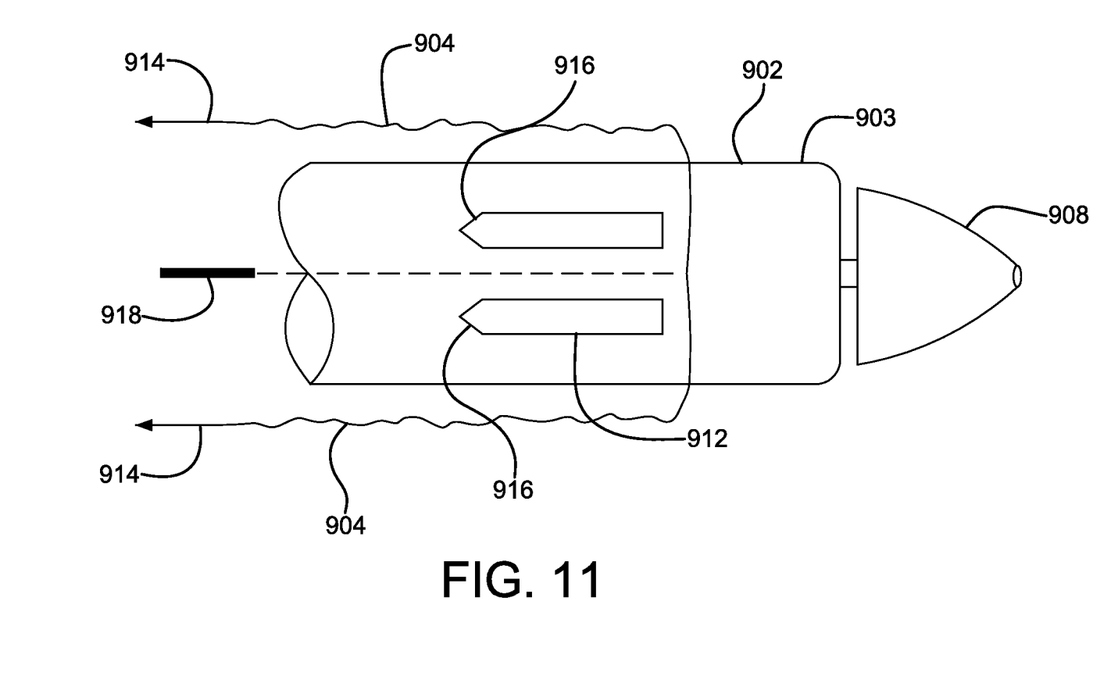
FIG. 11 is an enlarged perspective view of a catheter assembly incorporating the bridging member in FIG. 9 and a protective outer sleeve cutting blade.

A catheter assembly in accordance with various embodiments is shown illustratively in FIGS. 9-11. Referring to FIG. 9, a partial view of a proximal end of a delivery system 900 is shown for positioning a compacted medical device 902. The medical device 902 is constrained by a tubular sleeve 903 and is adjacent to a delivery catheter 906. Covering the compacted device 902 and the tubular sleeve 903 is a protective sleeve 904. The protective sleeve 904 provides a smooth outer surface to the delivery system 900, enhancing device positionability and compatibility with a distal hemostatic valve (not shown). Also shown is a catheter proximal tip 908. FIG. 10 is an enlarged view of the proximal end of the delivery system of FIG. 9. Shown is a compacted medical device 902, tubular constraining sleeve 903, a proximal catheter tip 908 and a protective outer sleeve 904. The protective outer sleeve 904 is shown releasably attached 909 to the proximal catheter tip 908. A gap 910 is shown between the proximal catheter tip 908 and the compacted medical device 902. A series of semi-rigid bridge straps 912 are shown spanning the gap 910. The bridge straps can be embedded into the protective outer sleeve 904. The bridge straps 912 provide a smooth transition between the proximal catheter tip 908 and the compacted medical device 902. The bridge straps 912 also allow the junction between the proximal catheter tip 908 and the compacted medical device 902 to flex when the delivery system 900 traverses torturous anatomy. Prior to device deployment, the protective outer sleeve 904 can be withdrawn by everting the sleeve back onto itself. The protective outer sleeve 904 can be everted by applying tension to the sleeve end as shown by direction arrows 914. The tension can be applied by pull lines or other means attached to the proximal end of the protective outer sleeve 904. When adequate tension is applied to the protective outer sleeve 904 the releasable attachment 909 is released allowing the sleeve to evert. The releasable attachment can be an adhesive join, or use other releasable attachment means as commonly known in the art. As further tension 914 is applied, the protective outer sleeve 904 further everts as shown in FIG. 11. The semi-rigid bridge straps 912 (embedded into the protective outer sleeve 904) bend and become reversed as shown in FIG. 11. The semi-rigid bridge straps 912 can optionally incorporate pointed or chamfered leading ends 916. The chamfered leading ends 916 will allow an optional cutting blade 918 to self-align to the gaps between the semi-rigid bridge straps 912 allowing the protective outer sleeve 904 to be longitudinally split. The split protective outer sleeve 904 can be subsequently fully removed from the catheter system. Semi-rigid bridge straps 912 can be fabricated from a variety of metallic or polymeric materials as commonly known in the art.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A catheter assembly comprising:
   a catheter having a proximal end and a distal end;
   an expandable device releasably attached to the catheter near the distal end, wherein the expandable device is maintained in a compressed state for endoluminal delivery;
   a tip fixedly secured to the distal end of and generally coaxial with the catheter; and
   a bridge member generally coaxial with the catheter and disposed in a gap between the expandable device and the tip, the bridge member being positioned distally to the expandable device and axially compressed between the tip and the expandable device such that the bridge member fills the gap between the expandable device and the tip with the expandable device maintained in the compressed state, such that the bridge member is configured to fill the gap between the expandable device and the tip during endolum inal delivery of the catheter assembly.

2. The catheter assembly as set forth in claim 1, further comprising a constraining sleeve that maintains the expandable device toward the outer peripheral dimension, wherein the bridge member is generally annular and includes a tapered surface radially engaging at least one of the expandable device and the constraining sleeve.

3. The catheter assembly as set forth in claim 2, wherein the tapered surface outwardly radially tensions at least one of the expandable device and the constraining sleeve.

4. The catheter assembly as set forth in claim 3, wherein the tapered surface is generally frustoconically shaped.

5. The catheter assembly as set forth in claim 1, wherein the catheter includes a lumen extending between the proximal and distal ends, the catheter assembly further comprising a tubular member extending through the lumen and having an end fixedly secured to the tip.

6. The catheter assembly as set forth in claim 5, wherein the tubular member includes a guidewire lumen extending axially therethrough.

7. The catheter assembly as set forth in claim 6, wherein the bridge member is generally annular and includes a bore which receives the tubular member therethrough.

8. The catheter assembly as set forth in claim 5, wherein a portion of the bridge member is fixedly secured to the tubular member so that a remaining portion of the bridge member is axially movable with respect to the catheter.

9. The catheter assembly as set forth in claim 1, wherein the bridge member fills the gap between the tip and the expandable device and provides a transition therebetween upon bending of the distal end of the catheter during deployment at an angled treatment site.

10. The catheter assembly as set forth in claim 1, wherein the bridge member is elastically deformed upon the axial compression between the tip and the expandable device.

11. The catheter assembly as set forth in claim 10, wherein the bridge member is axially movable with respect to the catheter.

12. The catheter assembly as set forth in claim 11, wherein at least a portion of the bridge member is fixedly secured to the tip or the catheter.

13. The catheter assembly as set forth in claim 1, wherein the catheter includes a guidewire lumen, and wherein the tip includes a bore generally axially aligned with the guidewire lumen to allow a guidewire to be fed through the catheter and the tip.

14. The catheter assembly as set forth in claim 1, further comprising a constraining sleeve that maintains the expandable device toward the outer peripheral dimension, wherein the bridge member includes a frustoconically shaped leading surface that faces the tip, which upon the axial compression between the expandable device and the tip provides a transition between the tip and the constraining sleeve.

15. The catheter assembly as set forth in claim 1, wherein the bridge member includes portions of varying durometer.

16. The catheter assembly as set forth in claim 1, wherein the bridge member includes a generally tubular shaped side wall and includes a wire frame coupled thereto to help the side maintain the gap between the tip and the device as the catheter assembly is bent during endoluminal delivery of the expandable device to a treatment site.

17. The catheter assembly as set forth in claim 1, wherein the bridge member fills the gap at an outer diameter of the catheter assembly.

18. The catheter assembly as set forth in claim 1, wherein the axial compression between the tip and the expandable device caused outward displacement of the bridge member to a desired outer profile.

19. The catheter assembly of claim 1, wherein the bridge member is disposed in the gap at a generally continuous diameter to fill the gap during endoluminal delivery of the catheter assembly.

20. A catheter assembly comprising:
   a catheter having a proximal end and a distal end;
   an expandable device releasably attached to the catheter near the distal end;
   a constraining sleeve that maintains the expandable device in a compressed state for endoluminal delivery;
   a tip fixedly secured to the distal end of the catheter; and
   a bridge member including a bore with the catheter within the bore, the bridge member being disposed in a gap distal to the expandable device and proximal to the tip, the bridge member being axially compressed between the tip and the expandable device such that a distal end of the expandable device is positioned proximal to a proximal end of the bridge member and the bridge member fills the gap at an outer diameter of the catheter assembly, such that the bridge member is configured to fill the gap at the outer diameter of the catheter assembly during endoluminal delivery of the catheter assembly.

21. The catheter assembly as set forth in claim 20, wherein the bridge member is elastically deformed from the axial compression between the tip and the expandable device causing outward displacement of the bridge member to fill the gap at the outer diameter of the catheter assembly.

* * * * *